(12) United States Patent
Lee et al.

(10) Patent No.: US 7,858,770 B2
(45) Date of Patent: Dec. 28, 2010

(54) SIRNA HAVING ANTIVIRAL ACTIVITY AGAINST NONPOLIO ENTEROVIRUS

(75) Inventors: Heuiran Lee, Seoul (KR); Yoo Kyum Kim, Seoul (KR); Hui Sun Lee, Seoul (KR); Jeonghyun Ahn, Seoul (KR)

(73) Assignee: University of Ulsan Foundation for Industry Cooperation, Mugeo-dong, Nam-gu, Ulsan (KR)

( * ) Notice: Subject to any disclaimer, the term of this patent is extended or adjusted under 35 U.S.C. 154(b) by 262 days.

(21) Appl. No.: 11/916,131

(22) PCT Filed: May 30, 2006

(86) PCT No.: PCT/KR2006/002073

§ 371 (c)(1),
(2), (4) Date: Nov. 30, 2007

(87) PCT Pub. No.: WO2007/026992

PCT Pub. Date: Mar. 8, 2007

(65) Prior Publication Data

US 2009/0298911 A1     Dec. 3, 2009

(30) Foreign Application Priority Data

Aug. 29, 2005   (KR) ................. 10-2005-0079184

(51) Int. Cl.
  C12P 19/34      (2006.01)
  C07H 21/02      (2006.01)
  C07H 21/04      (2006.01)
  A01N 43/04      (2006.01)
  C12Q 1/68       (2006.01)
(52) U.S. Cl. ................. 536/24.5; 435/6; 435/91.31; 514/44; 536/23.1; 536/24.32
(58) Field of Classification Search .............. 435/6, 435/91.1, 91.31, 455; 514/44; 536/23.1, 536/24.5, 24.32
See application file for complete search history.

(56) References Cited

U.S. PATENT DOCUMENTS

2002/0142293 A1 * 10/2002 Crainic et al. .............. 435/5

FOREIGN PATENT DOCUMENTS

WO    WO 02/103060    * 12/2002

OTHER PUBLICATIONS

Norder, H. et al., J. Gen'l. Virol., vol. 83, pp. 1721-1728 (2002).*
Reynolds, A. et al., Nature, Biotech., vol. 22, No. 3, pp. 326-330 (2004).*
Grist, N.R. et al., Enteroviruses in Human Disease, Porg. Med. Virol., v.24, pp. 114-157 (1978).
Muir, P., "Enteroviruses and heart disease," Br. J. Biomed. Sci., v.50, pp. 258-271 (1993).
Rotbart, H.A., "Enteroviral Infections of the Central Nervous System," Clin. Infect. Dis., v.20, pp. 971-981 (1995).
Dykxhoorn, E.M. et al., "Killing the Messenger: Short RNAs That Silence Gene Expression," Nat. Rev. Mol. Cell. Biol., v.4, pp. 457-467 (2005).
Fire, A. et al., "Potent and specific genetic interference by double-stranded RNA in Caenorhabditis elegans," Nature, v.391, pp. 806-811 (1998).
Elbashir, S.M. et al., "Duplexes of 21-nucleotide RNAs mediate RNAs interference in cultured mammalian cells," Nature, v.411, pp. 494-498 (2001).
Zamore, P.D. et al., "RNAi: Double-Stranded RNA Directs the ATP-Dependent Cleavage of MRNA at 21 to 23 Nucleotide Intervals," Cell, v.101, pp. 25-33 (2000).
Bernstein, E. et al., "The Rest is Silence," RNA, v.7, pp. 1509-1521 (2001).
Hasuwa, H. et al., "Small interfering RNA and gene silencing in transgenic mice and rats," FEBS LETT., v.532, pp. 227-230 (2002).
Dave, R.S. et al., "RNA interference: on the road to an alternate therapeutic strategy!," Rev. Med. Virol., v.13, pp. 373-385 (2003).
Stevenson, M., "Dissecting HIV-1 Through RNA Interference," Nat. Rev. Immunol., v.3, pp. 851-858, 2003.
Ahn, J. et al., "Characteristics of Apoptotic Cell Death Induced by Coxsackievirus B in Permissive Vero Cells," Intervirology, v.46, pp. 245-251, 2003.
Merl, S. et al., "Targeting 2A protease by RNA interference attenuates coxsackieviral cytopathogenicity and promotes survival in highly susceptible mice," Circulation, v.111(13), pp. 1583-1592, 2005.
Schubert, S. et al., "Maintaining Inhibition: siRNA Double Expression Vectors Against Coxsackieviral RNAs," J. Mol. Biol., v.346, pp. 457-465, 2005.
Yuan, J. et al., "Inhibition of coxsackievirus B3 replication by small interfering RNAs requires perfect sequence match in the central region of the viral positive strand," J. Virol., v.79(4), pp. 2151-2159, 2005.
van Regenmortel, M.H.V. et al., Taxonomic Structure of the Family, Virus Taxonomy, Academic Press, pp. 657-664, 2000.
Gitlin, L. et al., "Short interfering RNA confers intracellular antiviral immunity in human cells," Nature, v.418, pp. 430-434, 2002.
Gitlin, L. et al., "Poliovirus Escape from RNA Interference: Short Interfering RNA-Target Recognition and Implications for Therapeutic Approaches," J. Virol., v.79, pp. 1027-1035, 2005.
Graham, F.L. et al., "A New Technique for the Assay of Infectivity of Human Adenovirus 5 DNA," Virol., 52, pp. 456-467, 1973.
McCutchan, J.H. et al., "Enhancement of the Infectivity of Simian Virus 40 Deoxyribonucleic Acid with Diethyl-aminoethyl-Dextran," J. Natl. Cancer Inst., 41, pp. 351-357, 1968.
Chu, G. et al., "Electroporation for the efficient transfection of mammalian cells with DNA," Nucl. Acids Res., 15, 1311-1326, 1987.
Fraley, R. et al., "Introduction of Liposome-encapsulated SV40 DNA into Cells," J. Biol. Chem., 255, pp. 10431-10435, 1980.
Capecchi, M.R. et al., "High Efficiency Transformation by Direct Microinjection of DNA into Cultured Mammalian Cells," Cell, 22, pp. 479-488, 1980.
Felgner, P.L. et al., "Lipofection: A highly efficient, lipid-mediated DNA-transfection procedure," Proc. Nati. Acad. Sci. USA, 84, pp. 7413-7417, 1987.
Ahn, J. et al., "A small interfering RNA targeting coxsackievirus B3 protects permissive HeLa cells from viral challenge," J. of Virol., v.79(13), pp. 8620-8624, 2005.

* cited by examiner

Primary Examiner—Jane Zara
(74) Attorney, Agent, or Firm—Brooks Kushman P.C.

(57) ABSTRACT

The present invention relates to an siRNA (small interfering RNA) having antiviral activity against nonpolio enteroviruses, and a pharmaceutical composition comprising same as an active ingredient for preventing and treating diseases caused by nonpolio enterovirus infection.

6 Claims, 3 Drawing Sheets

SEQUENCE LISTING

```
<160> NUMBER OF SEQ ID NOS: 1

<210> SEQ ID NO 1
<211> LENGTH: 19
<212> TYPE: RNA
<213> ORGANISM: Artificial Sequence
<220> FEATURE:
<223> OTHER INFORMATION: A conserved sequence (called MET-2C) identified
      from a search of the entire viral genome sequences of CVA9, CVB1
      to CVB6, Echo6, and Echo 7, synthesized by DHARMACON as a 21
      nucleotide sequence duplex RNA molecule having dTdT 3'-overhang

<400> SEQUENCE: 1
aguccaaaug ccguauuga                                                 19
```

SIRNA HAVING ANTIVIRAL ACTIVITY AGAINST NONPOLIO ENTEROVIRUS

SEQUENCE LISTING

The text file hany0102pusa_ST25.txt, created Nov. 30, 2007, and of size 452 bytes, filed therewith, is hereby incorporated by reference.

FIELD OF THE INVENTION

The present invention relates to an siRNA (small interfering RNA) having antiviral activity against nonpolio enteroviruses, and a pharmaceutical composition comprising same as an active ingredient for preventing and treating diseases caused by nonpolio enterovirus infection.

BACKGROUND OF THE INVENTION

Nonpolio enterovirus, a member of the Picornaviridae family, is composed of VP1-4 structural proteins and a positive single-stranded RNA of about 7,400 bases as a genome, and the entire genome is translated as a single polypeptide from the 5' end thereof, which is cleaved by virus-encoded proteases into a set of individual proteins (see FIG. 1).

The enterovirus is a major causative agent which is responsible for a wide spectrum of human diseases ranging from mild aseptic meningitis to life-threatening dilated cardiomyopathy (see [Grist, N. R. et al., *Prog Med Virol*, 24:114-157, 1978; Muir, P., *Br J Biomed Sci*, 50:258-271, 1993; and Rotbart, H. A., *Clin Infect Dis*, 20:971-981, 1995]), but no effective preventive or therapeutic treatments against this virus infection are currently available.

RNA interference (RNAi) is a natural 'gene expression knock-down' process, which occurs in a sequence-specific manner (see [Dykxhoorn, D. M. et al., *Nat Rev Mol Cell Biol*, 4:457-467, 2005; and Fire, A. et al., Nature, 391:806-811, 1998]). This event involves a small interfering RNA (siRNA) of approximately 19-23 nt which specifically triggers catalytic degradation of complementary mRNAs via RNA-induced silencing complex (RISC) (see [Elbashir, S. M. et al., *Nature*, 411:494-498, 2001; Fire, A. et al.; and Zamore, P. D. et al., *Cell*, 101:25-33, 2000]).

There have accumulated numerous evidences showing that both chemically synthesized siRNAs and vectors expressing short hairpin RNAs (shRNA) can also induce RNAi in vitro and in vivo (see [Bernstein, E. et al., *Rna*, 7:1509-1521, 2001; Dykxhoorn, D. M. et al.; and Hasuwa, H. et al., *FEBS Lett*, 532:227-230, 2002]). Moreover, recent studies have suggested that RNAi can be used as a promising novel platform technology for the discovery of effective antiviral drugs (see [Dave, R. S. et al., *Rev Med Virol*, 13:373-385, 2003; and Stevenson, M., *Nat Rev Immunol*, 3:851-858, 2003]). These studies have consistently demonstrated that siRNAs are capable of effectively inhibiting the replication of a variety of viruses, such as hepatitis virus, poliovirus, or influenza virus under diverse experimental conditions. It was further demonstrated that siRNAs exhibit dramatic antiviral effects against coxsackievirus B3 (CVB3) in permissive cells (see [Ahn, J. et al., *Intervirology*, 46:245-251, 2003; Merl, S. et al., *Circulation*, 111:1583-1592, 2005; Schubert, S. et al., *J Mol Biol*, 346:457-465, 2005; and Yuan, J. et al., *J Virol*, 79:2151-2159, 2005]).

Yuan et al. examined the protective abilities of five CVB-specific siRNAs against CVB3 infection in both HeLa cells and murine cardiomyocytes, and found that the siRNA which targets viral protease 2A is the most effective (see Yuan, J. et al.).

Nonpolio enteroviruses include coxsackieviruses (CV) and echoviruses (Echo), which are CVA serotype (CVA1 to CVA3, CVA5 to CVA24), CVB serotype (CVB1 to CVB6), and 33 Echo serotypes (see [van Regenmortel, M. H. V. et al., *Virus taxonomy. Academic Press*, 2000]). In other words, nonpolio enteroviruses are characterized by: a number of distinct serotypes along with high genetic variability; high mutation rate during replication due to its lack of proof-reading capability; and ineffective siRNA manifestation when point mutations occur within the target region. Therefore, viral genome's variability and instability should be carefully considered in order to successfully utilize RNAi as antiviral therapeutics (see [Gitlin, L. et al., *Nature*, 418:430-434, 2002; and Gitlin, L. et al., *J Virol*, 79:1027-1035, 2005]).

Accordingly, the present inventors have endeavored to develop a multi-enteroviral targeting siRNA, which has a significant antiviral activity against a variety of nonpolio enteroviruses.

SUMMARY OF THE INVENTION

Accordingly, it is an object of the present invention to provide an siRNA having antiviral activities against nonpolio enteroviruses.

It is another object of the present invention to provide a pharmaceutical composition comprising said siRNA as an active ingredient and a pharmaceutically acceptable carrier for preventing and treating diseases caused by nonpolio enterovirus infection.

It is a further object of the present invention to provide a use of said siRNA in the manufacture of a medicament for preventing and treating diseases caused by nonpolio enterovirus infection.

In accordance with one aspect of the present invention, there is provided an siRNA having the following sequence:

AGUCCAAAUGCCGUAUUGA (SEQ ID NO.: 1).

In accordance with another aspect of the present invention, there is provided a pharmaceutical composition comprising said siRNA as an active ingredient and a pharmaceutically acceptable carrier for preventing and treating diseases caused by nonpolio enterovirus infection.

BRIEF DESCRIPTION OF DRAWINGS

The above and other objects and features of the present invention will become apparent from the following description of the invention taken in conjunction with the accompanying drawings, which respectively show:

FIG. 1: The structure of the viral genome of enterovirus and location of MET-2C siRNA with respect to its targeting region;

FIG. 2: The viability of cells infected with various serotype of reference nonpolio enterovirus strains after treating MET-2C siRNA (test group), and that of infected cells without MET-2C siRNA treatment (comparative group);

DETAILED DESCRIPTION OF THE INVENTION

Figure 3:
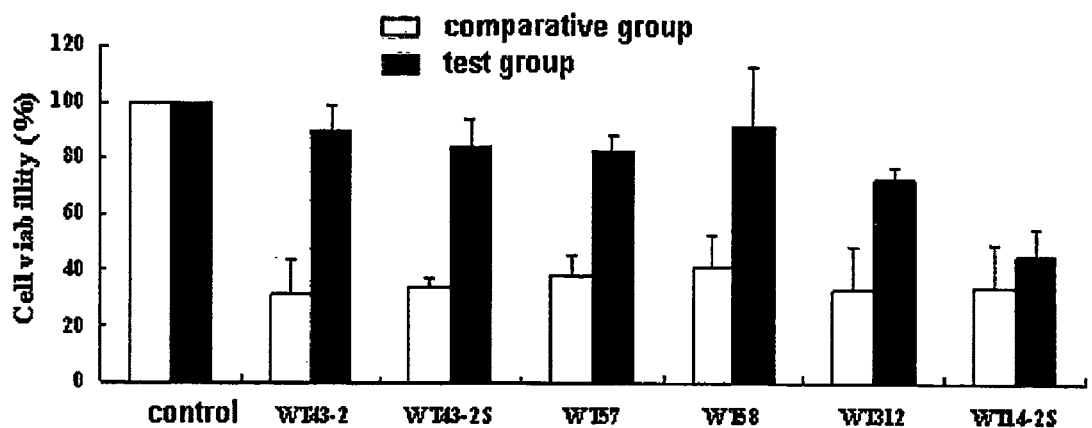
FIG. 3: The viability of cells infected with various serotype of wild-type nonpolio enterovirus strains after treating MET-2C siRNA (test group), and that of infected cells without MET-2C siRNA treatment (comparative group)

The inventive siRNA can be obtained by identifying an siRNA which recognizes the key conserved sequence existing in various enterovirus serotypes, e.g., CVA serotype (CVA1 to CVA3, CVA5 to CVA24), CVB serotype (CVB1 to CVB6), and 33 Echo serotypes, preferably CVA9, CVB1 to CVB6, Echo6 and Echo7.

The siRNA of the present invention, a 19-nucleotides duplex RNA, is located in the 2C cis-acting replication element (cre) of the virus genome, which is common among of the conserved sequences of nonpolio enteroviruses.

The present inventors designate said siRNA MET-2C (multi-enteroviral targeting-2C).

The MET-2C siRNA of the present invention can be used for preventing and treating diseases caused by nonpolio enterovirus infection.

Accordingly, the present invention provides a pharmaceutical composition comprising as an active ingredient and a pharmaceutically acceptable carrier for preventing and treating diseases caused by nonpolio enterovirus infection.

Further, the present invention provides a method for preventing and treating diseases caused by nonpolio enterovirus infection, comprising administering an effective amount of the siRNA according the present invention to a mammal. Preferably, the disease includes, but are not limited to, human diseases ranging from mild aseptic meningitis to life-threatening dilated cardiomyopathy.

The pharmaceutical compositions of the invention may be formulated for administration orally or parenterally, including intravenous, intraperitoneal, subcutaneous, rectal and topical routes of administration in accordance with conventional methods. In preparing the formulation, the active ingredient may be mixed or diluted with a carrier, or enclosed within a container type of carrier. In case that a carrier is used as a diluent, it may be a solid, semi-solid or liquid vehicle, an excipient or solvent of the active ingredient. Therefore, the formulation of the present composition may be in the form of a tablet, pill, powder, sachet, elixir, suspension, emulsion, solution, syrup, aerosol, soft and hard gelatin capsule, sterile injectable solution, sterile packaged powder and the like.

Representative examples of carriers, excipients and diluents are lactose, dextrose, sucrose, sorbitol, mannitol, calcium silicate, cellulose, methyl cellulose, microcrystalline cellulose, polyvinyl pyrrolidone, water, methyl hydroxybenzoate, propyl hydroxybenzoate, talc, magnesium stearate, mineral oil and the like. The formulation may additionally include fillers, anti-agglutinating agents, lubricating agents, wetting agents, flavoring agents, emulsifiers, preservatives and the like.

The compositions of the invention may be formulated so as to provide quick, sustained, or delayed release of the active ingredient after their administration to a mammal by employing any of the procedures known in the art.

MET-2C of the present invention or the composition thereof may be administered by any of the conventional methods for introducing a nucleotide into a cell in vitro and in vivo, such as calcium phosphate method, DEAE-dextran, electroporation, microinjection, and a method using virus or cationic liposome (see [[Graham, F. L. et al., *Virol.* 52, 456, 1973; McCutchan, J. H. et al., *J. Natl. Cancer Inst.* 41, 351, 1968; Chu, G. et al., *Nucl. Acids Res.* 15, 1311, 1987; Fraley, R et al., *J. Biol. Chem.* 255, 10431, 1980; Capecchi, M. R. et al., *Cell,* 22, 479, 1980; and Felgner, P. L. et al., *Proc. Nati. Acad. Sci. USA,* 84, 7413, 1987]. The commercially available method that uses cationic liposome is preferably used in the present invention.

The pharmaceutical composition of the present invention can be administered via various routes including oral, transdermal, subcutaneous, intravenous and intramuscular introduction in an effective amount ranging from about 10 mg/kg body weight, preferably 1 to 5 mg/kg body weight per day, in case of mammals including human, in a single dose or in divided doses. However, it should be understood that the amount of the active ingredient actually administered ought to be determined in light of various relevant factors including the condition to be treated, the chosen route of administration, the age, sex and body weight of the individual patient, and the severity of the patient's symptom. Therefore, the above dose should not be intended to limit the scope of the invention in any way.

The following Examples are intended to further illustrate the present invention without limiting its scope.

Example 1

Synthesis of an siRNA

A conserved sequence common for various enterovirus serotypes was searched from the entire viral genome sequence (NCBI; national center for biotechnology information, www.ncbi.nlm.nih.gov) of CVA9, CVB1 to CVB6, Echo6 and Echo7.

Figures 1, 2:
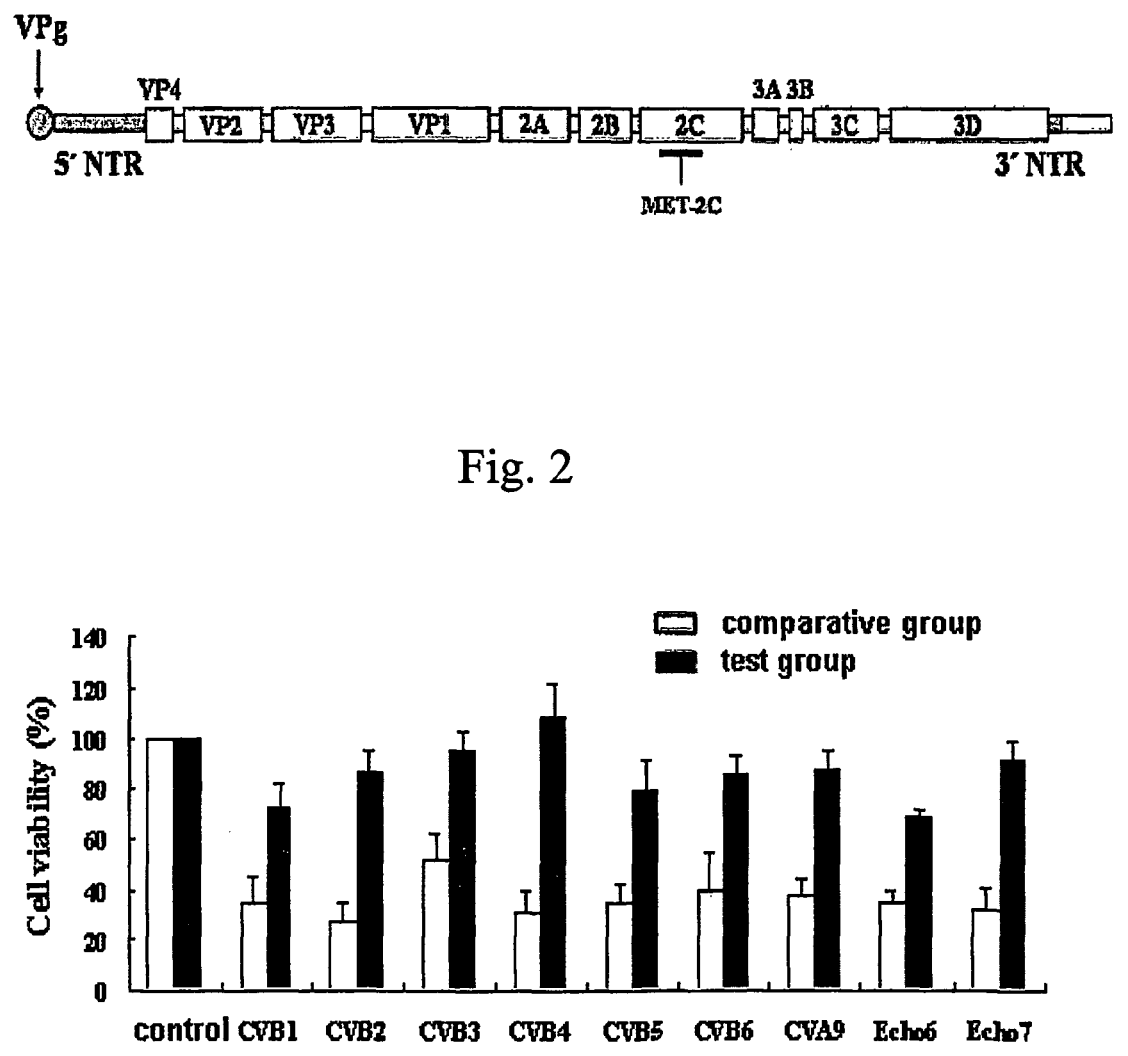

As a result, such a conserved sequence having 19 nucleotides was identified at 2C region, and it was designated MET-2C (see FIG. 1). The conserved sequence found for all the serotype examined is shown in Table 1.

TABLE 1

| Serotypes (Locus) | MET-2C (5'-AGUCCAAAUGCCGUAUUGA-3') | |
|---|---|---|
| | Sequence | Location |
| CVA9 (CXA9CG) | identical | 4435-4453 |
| CVB1 (CXA1G) | identical | 4392-4410 |
| CVB2 (AF081485) | identical | 4386-4404 |
| CVB3 (CXU57056) | identical | 4381-4399 |
| CVB4 (PICOXB4) | identical | 4386-4404 |
| CVB5 (AF114383) | identical | 4384-4402 |
| CVB6 (AF039205) | identical | 4376-4394 |
| Echo6 (AY302558) | identical | 4404-4422 |
| Echo7 (AF465516) | identical | 4413-4431 |

Subsequently, a 21-nucleotide duplex siRNA molecule of MET-2C having dTdT 3'-overhang was synthesized by DHARMACON (USA, www.dharmacon.com), and the prepared siRNA was designated MET-2C siRNA (SEQ ID NO: 1).

Test Example 1

Detection of the Protective Effect of Met-2C siRNA Against Reference Virus Strain The protective effect of MET-2C siRNA pretreatment against a reference virus strain was examined as follows.

(1-1) Cell Culture

HeLa cells were purchased from American Type Culture Collection (ATCC; USA), and the cells were cultured in Dulbecco's modified Eagle's medium supplemented with 10% fetal bovine serum, L-glutamine (2 mM), penicillin (100 IU/ml), and streptomycin (50 μg/ml) at 37° C. in a 5% $CO_2$ incubator.

(1-2) Virus Titration

Reference virus strains, CVA9, CVB1 to CVB6, Echo6 and Echo7, were purchased from ATCC (CVB1; VR-1032, CVB2; VR-29, CVB3; VR30, CVB4; VR-184, CVB5; VR-185, CVB6; VR-155, CVA9; VR-186, Echo 6; VR-36, Echo 7; VR-37), and each was examined by plaque assay as described in [Ahn, 5. J. et al., *Intervirology*, 46:245-251, 2003].

(1-3) Determination of Cell Viability Against Virus Infection

Each of the cells cultured in step (1-1) was added to each well of a 96-well plate at a concentration of $3 \times 10^4$ cells/well and transfected with 100 nM of MET-2C siRNA complexed with 0.25 μl of oligofectamine reagent (Invitrogen, USA) in 100 μl of OPTI-MEM medium (Invitrogen) without serum. 4 hours later, 50 μl of the growth media used in step (1-1) was added without removing the transfection mixture. After an additional 8 hours, the cells were infected with each reference viruses at 5 multiplicity of infection (MOI) per cell for 12 hours (Test group). Further, cells prepared by repeating the above procedure except for not pretreating MET-2C siRNA were used as a comparative group, and cells not treated with anything were used as a control group.

The cell viability of each group was measured by using MTT assay as follows:

20 μl of 3-(4,5-dimethylthiazol-2-yl)-2,5-diphenyl tetrazolium bromide (MTT, 5 mg/ml in PBS) in 100 μl of DMEM media supplemented with 10% fetal bovine serum was added to each well, and the cells were incubated in a $CO_2$ incubator at 37° C. for 4 hours. After discarding the media, 50 μl of dimethyl sulfoxide (DMSO) was added to each well and the cell content was mixed thoroughly to dissolve the dark blue crystals. The absorbance at 540 nm on an ELISA reader was monitored with the reference wavelength of 650 nm. The values thus obtained were applied to the following equation. The results are shown in FIG. 2 and Table 2:

$$\text{Viability (\%)} = \frac{\left(\begin{array}{c}\text{absorbance of the sample} - \\ \text{absorbance of the blank}\end{array}\right)}{\left(\begin{array}{c}\text{absorbance of the uninfected} - \\ \text{absorbance of the blank}\end{array}\right)} \times 100$$

TABLE 2

|  | Test group | Comparative group |
|---|---|---|
| Average viability (%) | 86.1 ± 8.1 | 35.9 ± 8.8 |

As can be seen in FIG. 2 and Table 2, the infected cells of the test group pretreated with MET-2C siRNA showed a dramatically enhanced cell viability against all serotypes of enterovirus infection, as compared with that observed for the infected cells of the comparative group received no MET-2C siRNA treatment.

Test Example 2

Detection of the Protective Effect of MET-2C siRNA Against Wild-Type Virus Strain The procedure of Test Example 1 was repeated except for using clinically isolated wild-type nonpolio enterovirus strains, CVB1, CVB5 and Echo6, purchased from the ATCC (CVB1: WT43-2, WT43-2S, WT57 and WT58; CVB5: WT312; and Echo6: WT14-2S) instead of reference virus strains in order to examine the protective effect of MET-2C siRNA pretreatment against a wild-type virus strain, and the results were shown in FIG. 3.

As can be seen in FIG. 3, the infected cells of the test group pretreated with MET-2C siRNA showed dramatically enhanced cell viability with all serotypes of enterovirus infection, as compared with that of the infected cells of the comparative group without MET-2C siRNA. Therefore, the inventive MET-2C siRNA has universal antiviral activity against diverse nonpolio enteroviruses.

Test Example 3

Observation of Change of Cell Morphology Caused by Antiviral Activity of Met-2C siRNA The cell infection was carried out by repeating the procedure of Test Example 1 except for using reference strains (CVB1, CVB5 and Echo6) and wild-type strains (WT43-2, WT312 and WT14-2S) in order to examine the morphological change of infected cells caused by antiviral activity of MET-2C siRNA. The infected cells were incubated with 1 μg/ml of membrane-permeable DNA-binding Hoechst 33342 dye (Molecular Prove, maintained as a stock solution of 10 mg/ml in $dH_2O$) for 30 min at 37° C. to dye nuclear of cells. The nuclear morphology was then examined using optical microscopy (Leica) and fluorescent microscopy (Leica) at an original magnification of 200×. The results are shown in FIG. 4.

Figure 4:
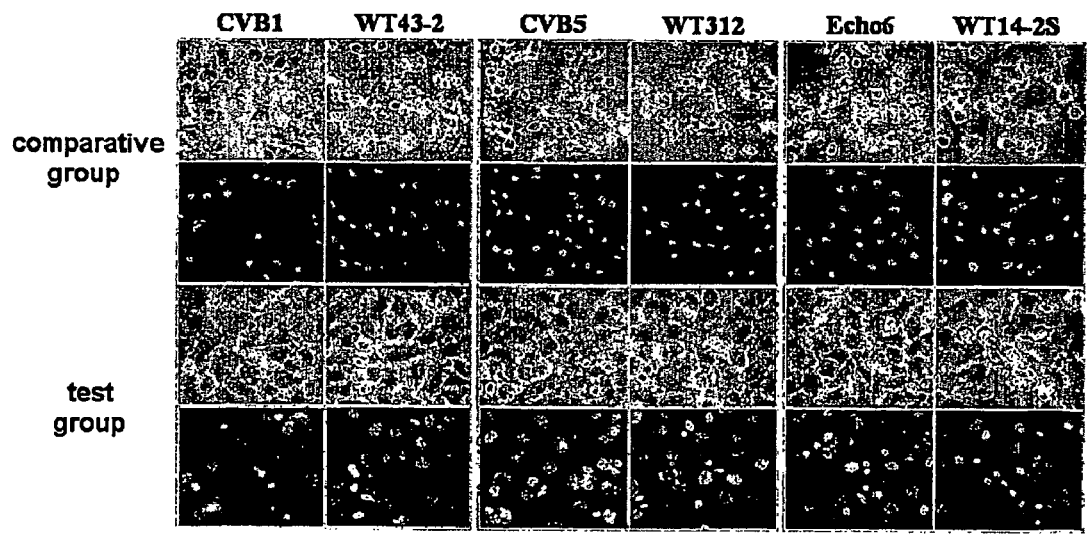
FIG. 4: The nuclear morphology of cells infected with various serotype of reference and wild-type nonpolio enterovirus strains after treating MET-2C siRNA (test group) as compared with that of infected cells without MET-2C siRNA treatment (comparative group)

As can be seen in FIG. 4, the infected cells of the comparative group without MET-2C began to detach from the culture plate and became round, and its nuclear condensation indicating progressing apoptosis was clearly noticed under Hoechst 33342 staining. By contrast, the infected cells of the test group pretreated with MET-2C siRNA were protected from viral cytotoxicity, and whenever the cells showed increased cell viability, the nuclear morphology thereof was normal.

Test Example 4

Observation of Change of Progeny Virus Production Caused by Antiviral Activity of Met-2C siRNA The cell infection was carried out by repeating the procedure of Test Example 1 except for using reference strain (CVB5) and wild-type strain (WT312) and infecting the strain with virus for 1 hour in order to examine the change of progeny virus production caused by antiviral activity of MET-2C siRNA. The virus inocula were thoroughly washed several times and the infected cells were further incubated for 11 hours after introducing with fresh media. The media and cells were harvested, the production of progeny virus was estimated by plaque assay as described in [Ahn, J. et al., supra]. The results are shown in Table 3.

TABLE 3

|  | Test group | | Control group | |
|---|---|---|---|---|
|  | CVB5 | WT312 | CVB5 | WT312 |
| Virus production (PFU/ml) | $7.9 \pm 0.2 \times 10^7$ | $8.1 \pm 0.2 \times 10^7$ | $6.8 \pm 0.4 \times 10^6$ | $7.0 \pm 0.3 \times 10^6$ |

As can be seen in Table 3, MET-2C siRNA significantly downregulate viral replication, which leads to inhibition of virus amplification.

Test Example 5

Observation of Change of Intracellular Ultrastructure Caused by Antiviral Activity of Met-2C siRNA The cell infection was carried out by repeating the procedure of Test Example 1 except for using reference strain (CVB5) in order to examine the ultrastructural change of infected cells caused by antiviral activity of MET-2C siRNA. The infected cells were recovered and fixed overnight in 4% glutaraldehyde at 4° C. The cells were then washed three times with 0.2 M cacodylate buffer (pH 7.2), post-fixed with 2% osmium tetraoxide for 1 hour at room temperature, and again washed three times in cacodylate buffer. The cells were stained en bloc for 1 hour at room temperature with 0.5% uranyl acetate, dehydrated through a graded ethanol/acetone series, and embedded in Mellenhauer's Epon-Araldite epoxy mixture No. 1 at 70° C. for 2 days. Ultrathin sections of the epoxy-embedded cells were obtained using a Sorvall MT5000 microtome and collected on 150-mesh copper grids. Each section was treated with 1% uranyl acetate for 2 hours, then stained with lead citrate for 30 min, and photographed in a Jeol 100CX transmission electron microscope. The results are shown in FIG. 5.

Figure 5:
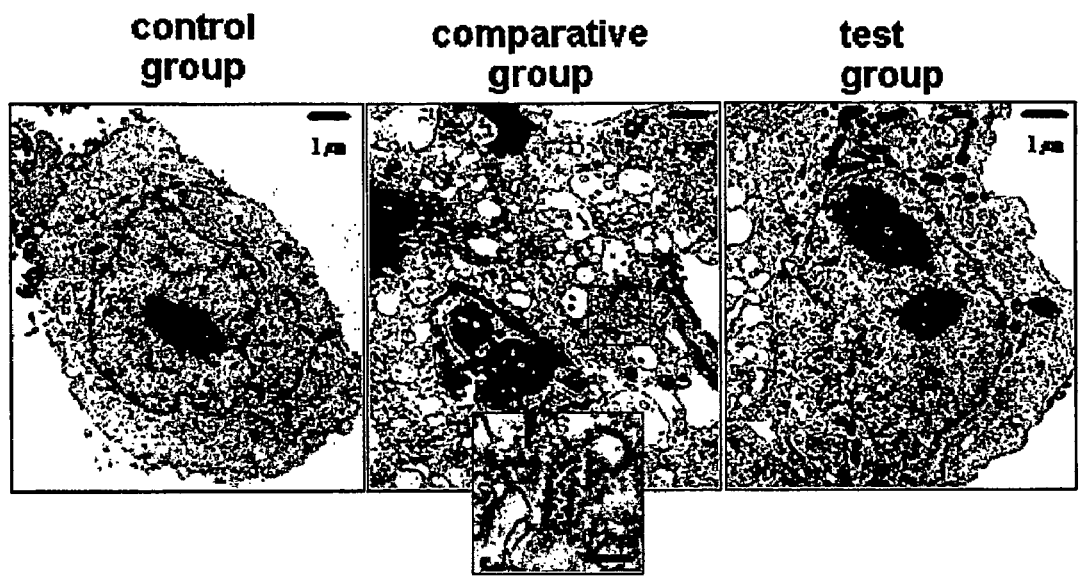
FIG. 5: The ultrastructure of cells infected with wild-type CVB2 virus strain after treating MET-2C siRNA (test group), and that of infected cells without MET-2C siRNA treatment (comparative group).

As can be seen in FIG. 5, the cytoplasm of the infected cells of the comparative group without MET-2C had progeny virus particles as honeycomb-shaped or lattered formation, while the cytoplasm of the infected cells of the test group pretreated with MET-2C siRNA was identical to that of the control group. Therefore, MET-2C siRNA exhibits an effective universal antiviral potency against a set of distinct serotypes of nonpolio enteroviruses by way of preventing or inhibiting the virus replication.

While the invention has been described with respect to the above specific embodiments, it should be recognized that various modifications and changes may be made and also fall within the scope of the invention as defined by the claims that follow.

What is claimed is:

1. An siRNA having the nucleotide sequence of SEQ ID NO: 1.

2. A pharmaceutical composition comprising the siRNA according to claim 1 as an active ingredient and a pharmaceutically acceptable carrier for preventing or treating diseases caused by nonpolio enterovirus infection.

3. The composition of claim 2, wherein the nonpolio enterovirus is coxsackievirus A, coxsackievirus B or echovirus.

4. An siRNA consisting of the nucleotide sequence of SEQ ID NO: 1.

5. A pharmaceutical composition comprising the siRNA according to claim 4 as an active ingredient and a pharmaceutically acceptable carrier for preventing or treating diseases caused by nonpolio enterovirus infection.

6. The composition of claim 5, wherein the nonpolio enterovirus is coxsackievirus A, coxsackievirus B or echovirus.

* * * * *